United States Patent
Knowles

[11] 3,944,586
[45] Mar. 16, 1976

[54] PREPARATION OF SALTS OF ANTIMONY (V) ESTERS
[76] Inventor: Richard Norris Knowles, Hockessin, Del. 19707
[22] Filed: Jan. 22, 1974
[21] Appl. No.: 435,495

Related U.S. Application Data
[62] Division of Ser. No. 204,704, Dec. 3, 1971, Pat. No. 3,836,557.

[52] U.S. Cl. ... 260/429 R; 106/15 FP; 260/45.75 R; 260/429.9; 260/446; 260/863
[51] Int. Cl.² ... C07F 3/08; C07C 31/28; C07F 9/90
[58] Field of Search ............. 260/446, 429 R, 429 J, 260/429.9

[56] References Cited
UNITED STATES PATENTS
3,221,035  11/1965  Silver .............................. 260/429 R
3,763,202  10/1973  Cumbo et al. ..................... 260/446

FOREIGN PATENTS OR APPLICATIONS
525,651  11/1926  Germany

OTHER PUBLICATIONS
Bourne et al., Chem. and Ind., (London), 1959, pp. 998–999.
Rosenheim et al., Benicht, 1925, 58, pp. 2000–2009.
Mann, The Heterocyclic Derivative of P, As, Sb, and Bi, Wiley–Interscience, N.Y., N.Y., 1970, pp. 611, 612, 620, 621.

*Primary Examiner*—Arthur P. Demers

[57] ABSTRACT

Water soluble salts of antimony (V) glycol esters are useful flame retardants for such meterials as textiles or polymeric resins. These flame retardants are applied together with a source of organic halogen. A typical such salt is tri(ethylenedioxy)hydrogen antimony (V), sodium salt.

4 Claims, No Drawings

PREPARATION OF SALTS OF ANTIMONY (V) ESTERS

This is a division of application Ser. No. 204,704, filed Dec. 3, 1971, now U.S. Pat. No. 3,836,557.

BACKGROUND OF THE INVENTION

This invention relates to novel, water-soluble, stable salts of antimony (V) glycol esters, useful as flame retardants.

Various antimony compounds have been used heretofore as flame retardants. The most commonly used compound is antimony trioxide. When used as a flame retardant for fabrics, antimony trioxide has the drawback of being insoluble in water or other common solvents, and it thus cannot be introduced within the fiber. Antimony trioxide applied to the outside of the fiber is subjected to mechanical wear and abrasion and is readily lost from the surface, unless special binders are used. These binders, such as ethylenevinyl acetate copolymer, make the fabric stiff and they are suitable only for use in tents, tarpaulins, etc.

Antimony (V) salts, such as antimony pentachloride, are decomposed by water with the liberation of the corresponding acid, such as hydrochloric acid. They are, therefore, unsuitable for use as flame retardants in many situations. Various antimonates, such as sodium antimonate or potassium antimonate, also are known; however, their low solubility in water limits their use. Antimony (V) esters also are known. Some of the esters are highly sensitive to moisture, decomposing readily in moist air. Several esters of antimony (III) and antimony (V) are disclosed in U.S. Pat. No. 3,031,425 to be useful flame retardants. While conventional antimony (V) esters are soluble in organic solvents and can be incorporated into organic polymers, they are less suitable for use in hydrophilic fibers or fabrics, such as cotton, which always contain water within the fibers.

There is a need, therefore, for water-stable, flame retardant antimony compositions which can be introduced into hydrophilic materials and can be insolubilized therein.

SUMMARY OF THE INVENTION

According to this invention, there are provided novel salts of antimony (V) glycol esters, which have the following Formula (1):

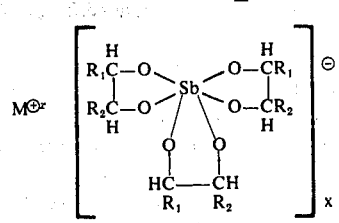

(1), wherein each of $R_1$ and $R_2$ independently is hydrogen or methyl; M is the cation of lithium, sodium, potassium, magnesium, calcium, strontium, barium, zinc, cadmium, guanidinium, ethylenediammonium, or ammonium having the following formula (2):

(2)

wherein each of $R_3$, $R_4$, and $R_5$ independently is hydrogen, methyl, ethyl, or 2-hydroxyethyl; and $x$ is the valence of the cation and has the value of 1 or 2.

The novel salts of antimony (V) esters of the present invention are useful flame retardants for textile materials or polymeric resins to which they are applied, provided a source of organic halogen also is present.

DETAILED DESCRIPTION OF THE INVENTION

The novel compounds of this invention are reasonably stable in water at room temperature above a pH of about 2.5. Below a pH of about 2.5, rapid hydrolysis of the esters occurs and antimony oxides precipitate. The preferred pH range, within which the novel compounds are most stable, is about 6–9. The stability in water of these compounds varies with the cation, the salts of univalent cations being more stable than the salts of divalent cations.

Representative salts of antimony (V) esters of the present invention include those listed below in Table I. They are named as salts of tri(alkylenedioxy)hydrogen antimony (V), i.e. the compound which would be obtained by substituting H for M in Formula (1), above.

TABLE I

| | |
|---|---|
| Tri(ethylenedioxy)hydrogen antimony (V) | , sodium salt |
| " | , lithium salt |
| " | , potassium salt |
| " | , zinc salt |
| " | , barium salt |
| " | , strontium salt |
| " | , calcium salt |
| " | , cadmium salt |
| " | , magnesium salt |
| " | , ammonium salt |
| " | , trimethylammonium salt |
| " | , guanidinium salt |
| " | , triethylammonium salt |
| tri(methylethylenedioxy)hydrogen antimony (V) | , sodium salt |
| " | , ammonium salt |
| " | , guanidinium salt |
| tri(ethylenedioxy)hydrogen antimony(V) | , ethanolammonium salt |
| tri(ethylenedioxy)hydrogen antimony(V) | , ethylenediammonium salt |
| tri(dimethylethylenedioxy)hydrogen antimony (V) | , sodium salt |

These salts can be characterized by their elemental composition and their nuclear magnetic resonance spectra, as shown in Examples 2–5, below. It is noteworthy that these salts are much more stable in water than the parent acids, which decompose extremely rapidly in water. A typical such acid is tri(ethylenedioxy)hydrogen antimony (V).

The stability in water of the novel salts of this invention also depends on the nature of the cation, the less amphoteric the cation the more stable being the salt. This can be shown by heating aqueous solutions of the salts. A comparison of the stability of several salts of tri(ethylenedioxy)hydrogen antimony (V) in distilled water is presented in Table II, below:

TABLE II

| Cation | Temperature at Which a Precipitate is Formed |
|---|---|
| $Na^+$ | No precipitate after 1 minute at 100°C |
| $Mg^{++}$ | Precipitate forms at about 90°C |
| $Ba^{++}$ | Precipitate forms at about 75°C |
| $Zn^{++}$ | Precipitate forms at about 65°C |

No precipitate forms when aqueous solutions of the ammonium and guanidium salts are heated for 1 minute at 100°C, indicating that the stability of these salts is comparable to that of the sodium salt.

The salts of these antimony (V) esters can be made by neutralization of the corresponding acids (hydrogen compounds) with appropriate bases, such as hydroxides or carbonates. The neutralization is carried out in a solvent that must satisfy the following two requirements:

1. the parent acid must be soluble in it, and
2. the addition of water, in amounts up to 30

Weight percent of the total solvent mixture, must not result in the formation of antimony oxide precipitates. The only solvents meeting these requirements are glycols with vicinal hydroxyl groups. In each case, the preferred solvent is the glycol used to make the ester. For example, ethylene glycol should be used for the tri(ethylenedioxy)esters and 1,2-dihydroxy propane for the tri(methylethylenedioxy) esters. This is preferred to avoid undesirable ester interchange.

The salts can be made in these solvents in the presence of up to about 30 weight percent of water, based on the total weight of the solvent mixture. When larger quantities of water are present, the base catalyzed hydrolysis of the ester interferes with the preparation of pure salts. When crystalline salts are to be isolated, it is usually preferred to keep the water content of the medium below about 15% by weight of the total solvent mixture.

During the neutralization reaction, the temperature of the solution should be kept below that at which the salt decomposes; usually, however, a temperature below 35°C. is preferred.

The starting acids (hydrogen compounds) are made by a reaction of antimony trioxide with appropriate glycol having vicinal hydroxyl groups and hydrogen peroxide to oxidize antimony to the pentavalent state. The reaction can be carried out by adding hydrogen peroxide to either (1) a slurry of antimony trioxide in the glycol or (2) a solution of an antimony (III) ester of the glycol. The preparation of tri(ethylenedioxy)hydrogen antimony (V) is described in Example 1, below, to illustrate this process.

The salts of divalent cations, which are less soluble than those of univalent cations, can also be made from the latter by metathesis with a soluble salt of the divalent cation in mixtures of vicinal hydroxyl glycols and water. By properly selecting the concentration and temperature, the divalent salt will precipitate and may be recovered in reasonably pure form.

These pentavalent antimony ester salts can be used in combination with an organic halogen source to impart flame retardancy to textiles and to various polymeric materials. When aqueous or alcoholic solutions of these salts are applied to cellulose-containing materials, antimony is carried into the fibers, where it can be insolubilized by heating or by lowering the pH to below about 2.5. The location of antimony oxides deep within the fiber makes them more resistant to laundering and weathering. The solid antimony oxides which precipitate are more finely divided and, hence, more efficient than commercial antimony trioxide as a flame retardant.

The preferred solvents for applying the novel antimony ester salts to cellulosic materials are water, ethylene glycol, 1,2-dihydroxypropane, 2,3-dihydroxybutane, and their mixtures. The source of halogen is best incorporated into the cellulosic material after solid antimony oxides have been precipitated.

Chlorwax 500 (a hydrocarbon containing about 60% chlorine, sold by Diamond Shamrock Corp.) and Dechlorane Plus 25 (a chlorinated organic compound sold by Hooker Chemical Co.) are examples of halogen sources that can be used with these pentavalent antimony ester salts on textiles. The halogen will be either chlorine or bromine.

These pentavalent antimony salts can be used at levels ranging from about 0.5 to 10% by weight, based on the finished article. Below 0.5% poor flame retardancy is observed, and above 10% additional improvements in flame retardancy are not sufficient to justify the higher cost. The amount of the halogen is from about 5% to 30% based on the weight of the finished article.

The dry pentavalent antimony ester salts can also be incorporated into various polymers such as halogenated polyester resins to enhance their flame retardancy. The finely ground salt is stirred thoroughly into a halogenated, unsaturated polyester, such as Diamond Shamrock's Dion resin. Benzoyl peroxide can then be added, and a solid polyester panel can be fabricated whose flame retardancy rating in the HLT-15 test is higher than in a panel made from the Dion resin alone. The HLT-15 test is described by R. E. McMahon et al., 25th Annual Technical Conference, 1970, Reinforced Plastics/ Composites Division of the Society of the Plastics Industry, Inc., in Section 9-C, pages 1–12.

It is not necessary to use an additional halogen source when the polymer itself already is halogenated. Other polymeric materials that can be made flame retardant by the process of the present invention include the following: halogenated polyurethanes, plasticized polyvinyl chloride, halogenated epoxy resins, and halogenated polycarbonates.

The following examples will serve to illustrate the pentavalent antimony ester salts, their method of synthesis and their use as flame retardant materials. In these examples, all percentages are by weight.

EXAMPLE 1

This example describes the preparation of crystalline tri(ethylenedioxy)hydrogen antimony (V) from antimony trioxide, ethylene glycol, and hydrogen peroxide. Seven hundred and ninety grams of H grade antimony trioxide supplied by the McGean Chemical Company of Cleveland, Ohio [5.43 moles of Sb (III)]and 3750 grams of ethylene glycol were added to a 5 liter round-bottom flask equipped with two dropping funnels, a mechanical stirrer, vacuum distillation apparatus, and a thermometer. The pressure of the system was reduced to 216 torr., and the slurry was heated vigorously. When the temperature reached about 150°C., the solution began to boil, liberating the water formed in the reaction of the ethylene glycol and the antimony trioxide. After about 45 minutes, 200 ml. of distillate was collected and the temperature rose to 160°C. At this point about ⅓ of the $Sb_2O_3$ had reacted.

The pressure of the system was reduced to 190 torr., and the dropwise addition of a 30.2% solution of hydrogen peroxide was started. Five hundred and thirty-six grams (4.75 moles $H_2O_2$) of hydrogen peroxide was added over a 3-hour, 13 minute period. During this period the water was removed continuously by distillation with about four parts of ethylene glycol per part water. This distillate contained about 100 ppm $H_2O_2$. Ethylene glycol was added to maintain the weight of the solution at about 4000 grams. As the oxidation and esterification reactions proceeded, more $Sb_2O_3$ reacted and dissolved. After about 60% of the peroxide was added, the solution became clear. The temperature of the solution remained between 145°C. and 150°C.

When the starting $Sb_2O_3$ contained orthorhombic crystals, filtration at this point was necessary in order to remove this insoluble material.

After this part of the addition was completed the solution was analyzed for Sb(III). The method was a potentiometric titration with a bromide-bromate solution of the sample dissolved in hydrochloric acid. The end point was determined by a sudden increase in the potential of a platinum-calomel electrode system. The solution of mixed Sb(III) and Sb(V) ethylene glycol esters was found to contain 156 grams of Sb(III) (1.27 moles). Thus, 4.16 moles of the starting Sb(III) were converted to Sb(V) by 4.75 moles of hydrogen peroxide; an 87.5% utilization of peroxide was realized. An additional 143 grams of 30.2% hydrogen peroxide (1.27 moles) was now added in a similar manner as the first portion. The solution was again analyzed and found to contain 70.5 gm. of Sb(III) (.63 mole). A 50% utilization of the peroxide was obtained in the second addition.

To complete the reaction, the solution was cooled to 110°C. and 70 grams of peroxide solution was added over a 1-minute period at atmospheric pressure. After 2 minutes the solution temperature was 122°C. This step converted about 70% of the remaining Sb(III) to Sb(V).

Then, the water and some excess ethylene glycol were removed by vacuum distillation. The pressure was gradually reduced to 5 torr., and the solution temperature was about 100°C. When the weight of solution was reduced to about 3500 gm. the Sb(V) ethylene glycol ester began to crystallize from the solution. Excess glycol was removed until the solids content of the slurry was so high that stirring became difficult. The weight of the slurry was 2220 grams, and its temperature was then about 120°C.

The vacuum was released and 1200 ml. of tetrahydrofuran was added to dilute the slurry and to facilitate its filtration. The crystals were filtered under a blanket of dry nitrogen. The wet crystals were then washed with 2.5 liters of tetrahydrofuran and dried at room temperature with a stream of dry nitrogen. Fourteen hundred and sixty-nine grams of tri(ethylenedioxy)hydrogen antimony (V) were obtained. The crystalline product contained 40.5% Sb(V) and 0.025% Sb(III). The Sb(V) was determined by dissolving the crystals in hydrochloric acid, adding potassium iodide and titrating the liberated iodine with sodium thiosulfate solution. (Details of the analytical procedure are given in Standard Methods of Chemical Analysis published by D. Van Nostrand and Co., Inc., Princeton, N.J., pp. 75–76, 1939.)

The Sb(III) was analyzed according to the procedure given earlier in this example.

Calc'd. for $C_6H_{13}O_6Sb$: C, 23.8, H, 4.3: Sb, 40.3%. Found: C, 23.9; H, 4.3; Sb, 40.6%.

To complete the material balance, the mother liquor was titrated and found to contain 23.8 grams of Sb(III) and 34.5 grams of Sb(V). Thus, 99% of the antimony charged was accounted for and 90.0% of it was converted to crystalline tri(ethylenedioxy) hydrogen antimony (V).

EXAMPLE 2

The tri(ethylenedioxy)hydrogen antimony (V), sodium salt was prepared as follows.

Tri(ethylenedioxy)hydrogen antimony (V) (150 g; 0.497 mole) was dissolved in a solution consisting of 650 g of ethylene glycol and 80 g of distilled water. The pH of this solution was 0.4. A 50% aqueous sodium hydroxide solution (38.5 g; 0.480 mole) was added slowly to the stirred solution over a 40 minute period; the temperature was kept between 29° and 35°C with gentle cooling. At this time, the pH was 6.9. Crystals of tri(ethylenedioxy)hydrogen antimony (V), sodium salt began to separate near the end of the sodium hydroxide addition. Approximately forty minutes after the end of the sodium hydroxide addition a thick slurry of crystals was present. The slurry was cooled to 0°–5°C, held at that temperature for thirty minutes, and then filtered. The white, crystalline product was washed with acetone and dried under nitrogen. The yield was 79.2% of crystals melting at 128.5°–130.0°C.

Calc'd. for $C_6H_{12}NaO_6Sb.3$ ethylene glycol: C, 28.2; H, 5.9; Na, 4.5; O, 37.6; Sb, 23.8%. Found: C, 28.1; H, 6.0; Sb, 23.8%.

N.M.R. and I.R. spectroscopic data for this salt are given in Table III of Example 5.

When this salt was subsequently dried over phosphorus pentoxide at 110°C. and 0.2 mm of mercury, the three ethylene glycol moles of crystallization were removed. The resulting crystals were distinctly hexagonal. They appeared to sinter at about 180°C., but did not melt below 260°C.

Calc'd for $C_6H_{12}NaO_6Sb$: C, 22.2; H, 3.7; Na, 7,1; O, 29.6; Sb, 37.4%. Found: C, 21.9; H, 4.4; Sb, 37.7%.

EXAMPLE 3

To a solution of tri(ethylenedioxy)hydrogen antimony (V), sodium salt (37.2 g; 0.104 mole) in a mixture consisting of 650 g of ethylene glycol and 80 g of water was added 14.2 g of a 50% aqueous zinc chloride solution (7.1 g active; 0.052 mole). The solution was placed in a refrigerator at about 5°C for three days. The crystals which separated were filtered, washed sequentially with acetone and diethyl ether, and then dried under nitrogen. The dense, white crystals (12.0 g) melted at 154°–157°C.

Calc'd for $C_{12}H_{24}O_{12}Sb_2Zn.7H_2O$: C, 18.3; H, 4.8; O, 38.2; Sb, 30.6; Zn, 8.2%. Found: C, 18.3; H, 4.7; Sb, 29.5; Zn, 8.2%.

N.M.R. and I.R. spectroscopic data for this salt are given in Table III of Example 5.

EXAMPLE 4

A solution of tri(ethylenedioxy)hydrogen antimony (V) (5.0 g; 0.0166 mole) in a mixture of 23 g of ethylene glycol and 3 g of water was prepared. Guanidine carbonate (1.50 g; 0.0083 mole) was added with stirring. When carbon dioxide evolution ceased, the solution was left standing at room temperature for three days. The fine needles which separated were filtered and washed with ether. The melting point was higher than 260°C.

Calc'd. for $C_7H_{18}N_3O_6Sb.2H_2O$: C, 21.1; H, 5.7; N, 10.6; Sb, 30.6%. Found: C, 21.6; H, 4.7; N, 10.6; Sb, 31.1%.

N.M.K. and I.R. spectroscopic data for this salt are given in Table III of Example 5.

EXAMPLE 5

The N.M.R. spectra of the salts of this invention support the assigned structure of these salts. In Table III are spectral data for the sodium, zinc, and guanidine salts, along with the free acid for comparison. Hexadeuterodimethyl sulfoxide was used as the solvent and tetramethylsilane (TMS) was used as the internal standard. All peak positions are repeated as δ from TMS.

TABLE III

| Compound | Peak Multiplicity | Relative Area | Assignment |
|---|---|---|---|
| Free Acid | 5.72 Singlet | — | Acidic hydrogen |
| | 3.65 Singlet | — | Hydrogens in ethylenedioxy bridges |
| | 3.45 Singlet | — | Hydrogens in ethylene glycol methylenes (trace of ethylene glycol present) |
| Sodium Salt .$3C_2H_6O_2$ | 4.50 Broad singlet | 18 | Ethylene glycol of crystallization |
| | 3.52 Singlet | 56 (equal) | Hydrogens in ethylenedioxy bridges (the addition of several drops of water moved the 4.50 peak under the 3.52 peak, and the spectrum became identical with that of the zinc salt shown below) |
| | 3.41 Singlet | | |
| Zinc Salt | 3.52 Singlet (broadened base) | | Hydrogens in ethylenedioxy bridges with $H_2O$ of crystallization under 3.52 peak. |
| | 3.42 Singlet (3.52 peak much larger than 3.42 peak) | | |
| Guanidine Salt | 4.61 Singlet | 32 | Guanidine hydrogens and hydrated water |
| | 3.66 Broad singlet | 44 | Hydrogens in ethylenedioxy bridges. |
| | 3.58 Singlet | | |
| Ethylene Glycol | 4.60 Singlet | 42 | Hydroxyl hydrogens |
| | 3.45 Singlet | 81 | Methylene hydrogens |
| Sodium Salt | 3.52 Singlet | | Hydrogens in ethylenedioxy bridges. |

The I.R. spectra of the salts of this invention have four or five highly characteristic bands in the 850–1200 $cm^{-1}$ region; the data are summarized in Table IV. The most notable spectral change is the shift of 1088 $cm^{-1}$ ethylene glycol peak to the 1105–1108 $cm^{-1}$ region; this peak also becomes much weaker.

TABLE IV

| Compound | Peak ($cm^{-1}$) | Order of Intensity (the lowest number denotes the highest intensity) |
|---|---|---|
| Ethylene glycol | 1088 | 1 |
| | 1040 | 1 |
| | 885 | 2 |
| | 865 | 3 |
| Sodium salt .$3C_2H_6O_2$ | 1105 | 4 |
| | 1075 | 2 |
| | 1038 | 1 |
| | 895 | 3 |
| | 877 | 2 |
| Zinc salt | 1108 | 4 |
| | 1040 | 1 |
| | 898 | 2 |
| | 877 | 3 |
| Guanidine Salt | 1108 | 4 |
| | 1033 | 1 |
| | 890 | 3 |
| | 875 | 2 |
| Sodium Salt | 1105 | 3 |
| | 1088 | 3 |
| | 1038 | 1 |
| | 890 | 2 |

EXAMPLE 6

The potassium salt of tri(ethylenedioxy)hydrogen antimony (V) can be prepared according to the method of Example 2 by substituting potassium hydroxide for sodium hydroxide.

EXAMPLE 7

The magnesium salt of tri(ethylenedioxy)hydrogen antimony (V) can be prepared according to the method of Example 3 by substituting magnesium chloride for the zinc chloride.

EXAMPLE 8

The ammonium salt of tri(ethylenedioxy)hydrogen antimony (V) can be prepared according to the method of Example 4 by substituting ammonium carbonate for the guanidine carbonate.

EXAMPLE 9

The tri(methylethylenedioxy)hydrogen antimony (V), sodium salt can be prepared according to the method of Example 2 by substituting tri(methylethylenedioxy)hydrogen antimony (V) for the triethylenedioxy hydrogen antimony (V), and 1,2-dihydroxypropane for the ethylene glycol.

EXAMPLE 10

The tri(ethylenedioxy)hydrogen antimony (V), (150 g; 0.497 mole) can be dissolved in a mixture consisting of 650 g of ethylene glycol and 80 g of distilled water. This solution can be further diluted with 130 g of distilled water. This solution can then be treated with 38.5 g of a 50% aqueous sodium hydroxide solution according to Example 2; the triethylenedioxy hydrogen antimony (V), sodium salt is formed.

EXAMPLE 11

The barium salt of tri(ethylenedioxy)hydrogen antimony (V) can be prepared according to the method of Example 3 by substituting barium chloride for the zinc chloride.

EXAMPLE 12

A 10 g sample of tri(ethylenedioxy)hydrogen antimony (V), sodium salt (0.031 mole) was dissolved in 17 ml of distilled water at room temperature; this was a 37% by weight solution. This solution was stirred while 4.2 g of a 50% aqueous zinc chloride (0.015 mole) solution was added dropwise over a period of several minutes. A white precipitate began to form shortly after the first few drops of the zinc chloride solution had been added. The slurry was stirred for ten minutes, and then it was filtered. The solids were washed sequentially with 10 ml of water and 50 ml of acetone. The dry crystals had the same melting point and spectra as the salt prepared in Example 3.

EXAMPLE 13

A 7.0 × 25.4 cm sample of 80 × 80 cotton print cloth was padded to a 100% add-on with a 16% solution of (triethylenedioxy)hydrogen antimony (V), zinc salt in ethylene glycol. The fabric was dried in a forced draft textile curing oven at 149°C (300°F) for 2 minutes. The fabric was then placed in an atmosphere of steam for ten minutes. The fabric was then dried at 79°C (175°F) for 1 minute and allowed to equilibrate with the atmosphere. The fabric had a 16.1% pick-up of the antimony salt. The fabric was then washed for 5 minutes in cold water, dried and weighed again after equilibration. The fabric still contained 12.3% of the antimony compound. The fabric was white after this test.

In a similar experiment, a sample of 80 × 80 cotton cloth was padded to a 100% add-on with a 16% slurry of antimony trioxide. The fabric was dried for 2 minutes at 149°C (300°F). The fabric was allowed to equilibrate with the atmosphere; the add-on was 11.5%. The fabric was then washed in cold water for 5 minutes, dried and weighed again after equilibration. The fabric contained 2.8% antimony compound. The fabric was white after this test.

These two tests show that the antimony oxides deposited within the fiber by the tri(ethylenedioxy)hydrogen antimony (V), zinc salt treatment are more difficult to remove than the antimony trioxide deposited on the surface of the fibers.

EXAMPLE 14

Suitable flame retarded fabric can be prepared by treating fabric first with tri(ethylenedioxy)hydrogen antimony (V), zinc salt according to Example 13. The fabric can then be coated with an emulsion consisting of 75% Chlor 500 (a liquid, chlorinated hydrocarbon) and 25% Elvax (an ethylene-vinylacetate copolymer). The application rate of this emulsion is adjusted to give an add-on of approximately 20%. This fabric will then pass the American Association of Textile Chemists and Colorists vertical flame test 34–1969.

EXAMPLE 15

In another flame retardant application tri(ethylenedioxy)hydrogen antimony (V), zinc salt was ground to pass a 60 mesh screen. This powder (1.5 g) was then stirred thoroughly into 50 g of Dion FR6399 (a brominated, unsaturated polyester resin formulation sold by Diamond Shamrock Co.). This combination was stirred for 20 minutes at 35°–40°C. Then 0.5 g of benzoyl peroxide was added, and the mixture was stirred at 42°C for 20 minutes. This mixture was then poured into a mold, and pressed at 29,000 psi on the 2.56 in. diameter (6.50 cm) piston according to the following heating schedule:

| Time | Temperature |
|---|---|
| 15 minutes | 69°C (175°F) |
| 20 minutes | 107°C (225°F) |
| 20 minutes | 135°C (275°F) |

The press was then cooled to 121°C (250°F) with air, and then to 65°C (149°F) with water before removing the mold.

The panel was cut into test samples and tested in the HLT-15 flammability test. It had a rating of 100, whereas samples made from the untreated resin had a rating of only 80. In this test, a higher bating corresponds to a better flame resistance of the material.

I claim:

1. A process for the preparation of a compound of the formula

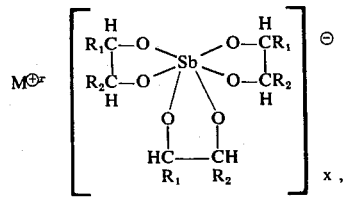

wherein
each of $R_1$ and $R_2$ independently is hydrogen or methyl:
M is the cation of lithium, sodium, potassium, magnesium, calcium, strontium, barium, zinc, cadmium, guanidinium, ethylenediammonium, or ammonium having the following formula

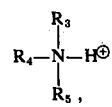

wherein
each of $R_3$, $R_4$, and $R_5$ independently is hydrogen, methyl, ethyl or 2-hydroxyethyl; and
$x$ is the valence of the cation and has the value of 1 or 2;
said process comprising the reaction of the compound of formula $H^\oplus$ 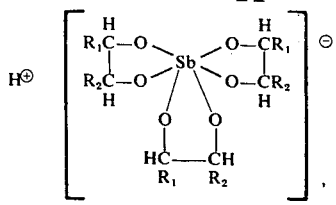

with the hydroxide or carbonate of the cation $M^{\oplus x}$ in a glycol containing vicinal hydroxy groups, at a temperature below the decomposition temperature of the resulting salt; in the presence of 0–30 weight percent of water based on the total solvent mixture.

2. The process of claim 1 wherein the water content of the solvent is 0–15 weight percent of the total solvent mixture.

3. The process of claim 1, wherein the solvent is at least one of ethylene glycol and 1,2-dihydroxypropane.

4. A process for the preparation of a compound having the formula

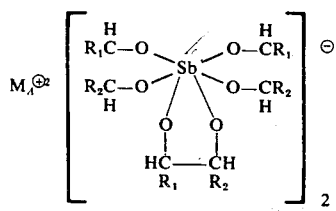

said process comprising a metathetic exchange between a compound of the formula

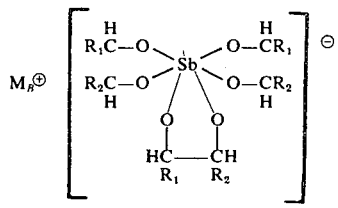

and a soluble salt of the cation $M_A^{\oplus 2}$ in a solvent consisting of a mixture of 0–70% by weight of a glycol containing vicinal hydroxyl groups and 30–100% by weight of water;

each of $R_1$ and $R_2$ being independently hydrogen or methyl;

$M_A$ being the cation of magnesium, calcium, strontium, barium, zinc, or cadmium; and $M_B$ being the cation of lithium, sodium, potassium, or ammonium.

* * * * *